United States Patent [19]

Weintraub

[11] Patent Number: 4,774,267
[45] Date of Patent: Sep. 27, 1988

[54] DENTAL MATERIAL COMPRISING ADDUCT OF GLYCIDILMETHACRYLATE AND TRICARBOXYLIC ACID

[75] Inventor: Yuri Weintraub, Forest Hills, N.Y.

[73] Assignee: IPCO Corp., White Plains, N.Y.

[21] Appl. No.: 81,715

[22] Filed: Aug. 4, 1987

[51] Int. Cl.$^4$ .................... C08K 3/00; A61K 6/08; C08F 18/00; C08F 18/14
[52] U.S. Cl. ................... 523/116; 523/115; 523/117; 522/100; 522/104; 526/320; 526/323
[58] Field of Search ............... 523/116, 117, 115; 526/320, 323; 522/100, 104

[56] References Cited

U.S. PATENT DOCUMENTS 4,517,327  5/1985  Heaps ...................... 525/155
4,691,045  9/1987  Fukuchi et al. ............ 526/318

OTHER PUBLICATIONS

Chem. Abs 84-91884q Matsuzaka et al., (J 7589504) Jul. 1975.
Derwent Abs. 77-42175y/24 Nippon Osus Aug. 1975.

*Primary Examiner*—Herbert J. Lilling
*Attorney, Agent, or Firm*—Helfgott & Karas

[57] ABSTRACT

Dental restorative compositions comprising a polymerizable polyfunctional prepolymer type methacrylate having the following chemical formulas:

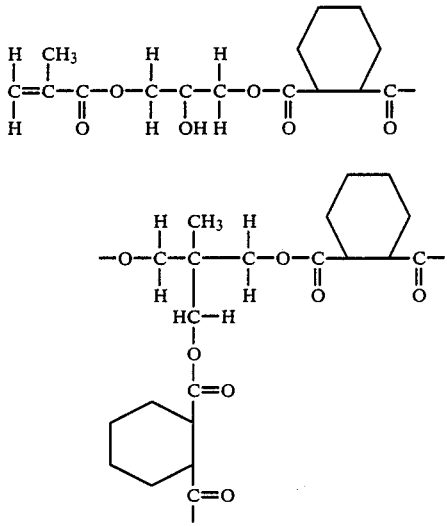

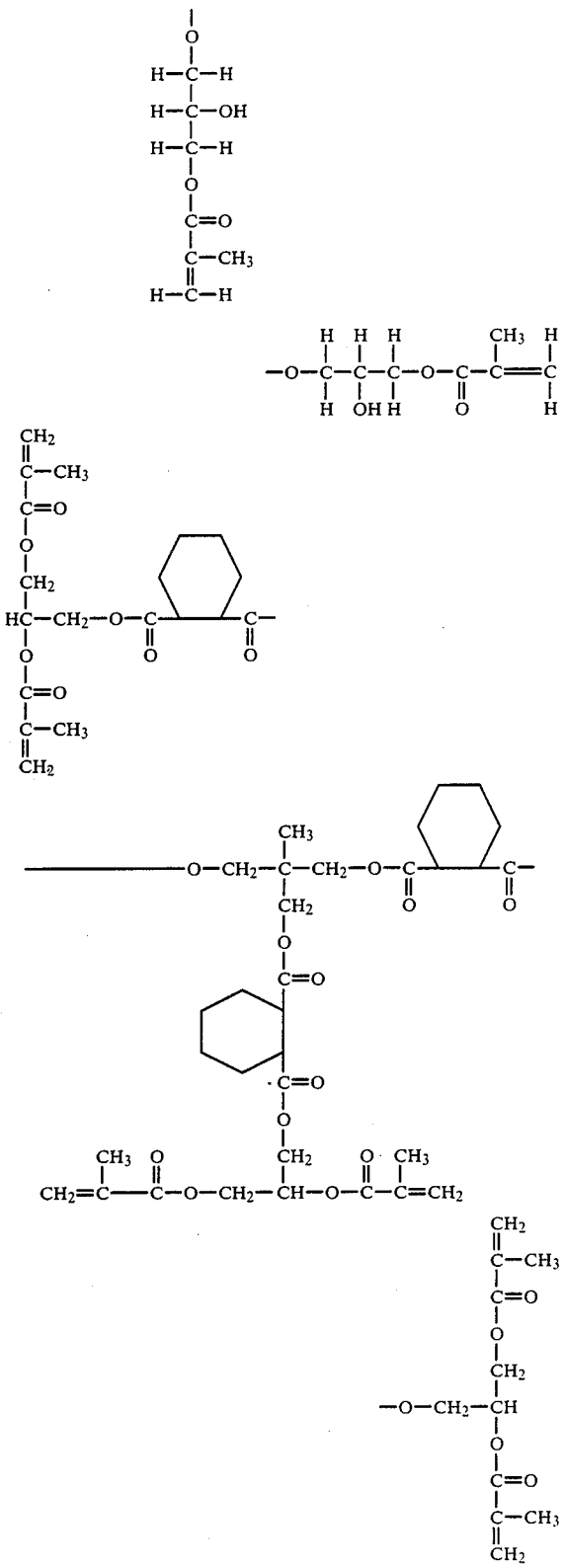

and a filler material, are disclosed. The prepolymer monomers and polymer formed are also taught.

8 Claims, No Drawings

DENTAL MATERIAL COMPRISING ADDUCT OF GLYCIDILMETHACRYLATE AND TRICARBOXYLIC ACID

FIELD OF THE INVENTION

The present invention relates to the use of poly functional prepolymer type methacrylates having the following chemical structures:

BACKGROUND OF THE INVENTION

In recent years the use of polymer based dental materials has gained in prominence, since these materials have improved physical and mechanical properties and provide dental restorations having superior durability. These materials have been found to be particularly useful as filled restorative materials, bonding agents, tissue scalers and orthodontic adhesives, particularly

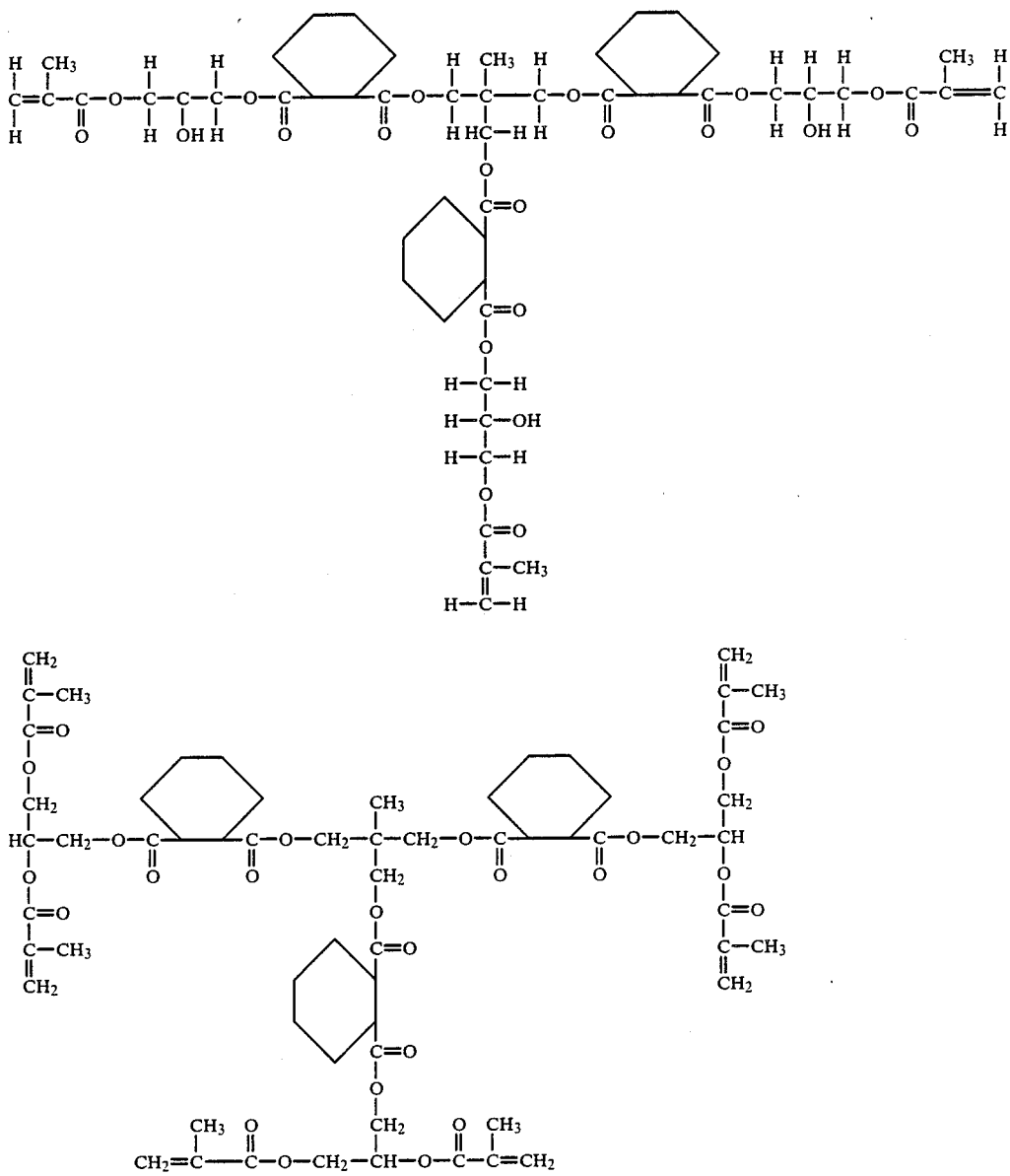

and dental compositions comprising one or more of these materials.

those materials based upon polymerizable aromatic and aliphatic methacrylates, which polymerize in situ, most with the application of visual light.

The best properties in these types of materials have been obtained when the resin part of the composition is comprised of one or more of the following monomers:

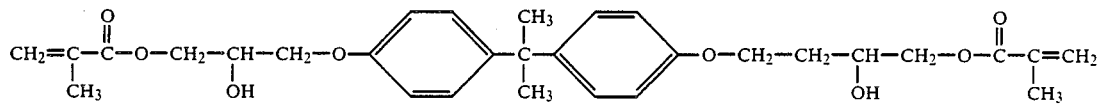

2,2-bis-[4'-(3''-methacroyl-2''-hydroxypropoxy)-phenyl]propan, known in industry as BIS-GMA, its adduct with various alkyl iso, or diisocyanates, such as the adduct described in Waller U.S. Pat. No. 3,629,187 and urethane dimethacrylates as are described, for example, in the U.S. Pat. Nos. 3,425,988; 3,709,866 and 3,629,187 and the like; and

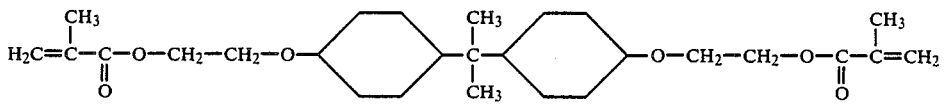

i.e. 2,2-bis(4'(2''-methacroylethoxy)phenyl)propane, known in industry as EBA.

In addition to the aforementioned references various polymeric dental materials have been described in the following U.S. Pat. Nos.: 3,066,112 (Bowen); 3,179,623 (Bowen); 3,194,783 (Bowen); 3,194,784 (Bowen); 3,539,533 (Lee II et al.); 3,541,068 (Taylor); 3,597,389 (Taylor); 3,721,644 (Stoffey et al.); 3,730,947 (Stoffey et al.); 3,751,399 (Lee Jr. et al.); 3,766,132 (Lee Jr. et al.); 3,774,305 (Stoffey et al.); 3,860,556 (Taylor); 3,862,920 (Foster et al.); 3,926,906 (Lee II et al.); 4,102,856 (Lee Jr.); 4,107,845 (Lee Jr. et al.); 4,490,115 (Orlowsky et al.); 4,544,359 (Waknine); 4,536,523 (Antonucci); 4,551,486 (Tateosian); 4,552,906 (Podszun); 4,553,940 (Koblitz et al.).

SUMMARY OF THE INVENTION

The present invention provides polymerizable prepolymer type of polyfunctional methacrylic monomers which are particularly useful in dental restorative compositions, which have improved physical and mechanical characteristics and higher crosslinked densities when compared with BIS-GMA. It has been discovered that significantly improved resins which are useful as binders in dental restorative compositions are obtained from monomer compounds of the following formula:

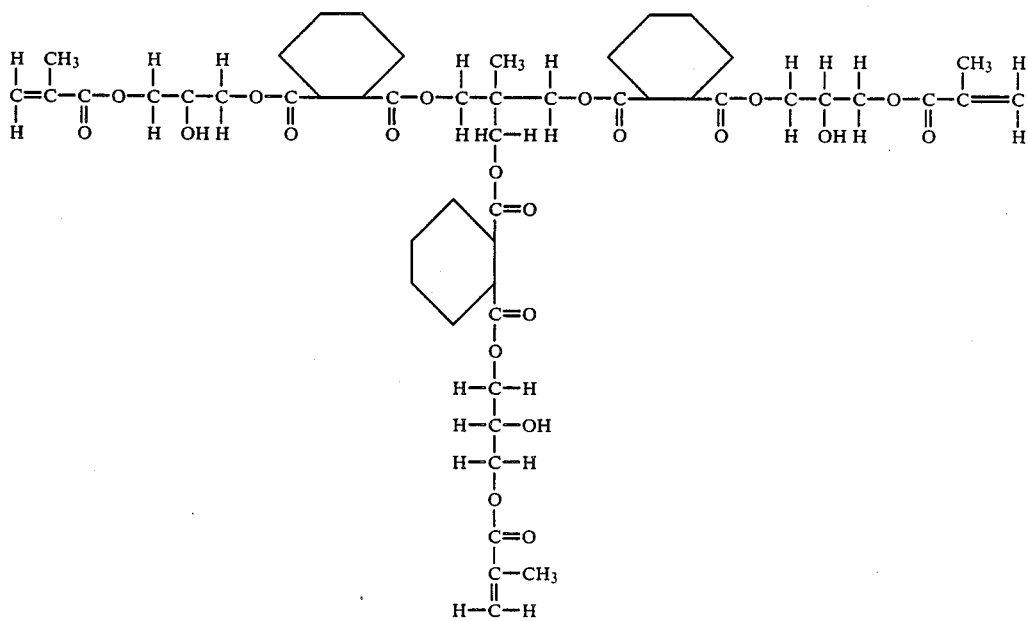

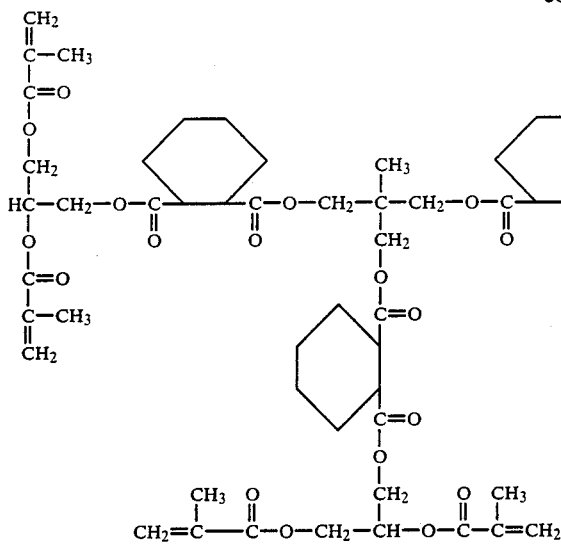

-continued

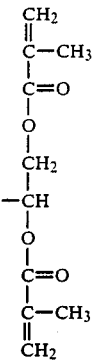

This invention also relates to dental restorative compositions comprising the monomers disclosed.

DETAILED DESCRIPTION OF THE INVENTION

This invention relates to polyfunctional methacrylate compounds represented by the prepolymer branched structure obtained in two stages. In the first stage the reaction between anhydrids such as phtalic, tetrahydro or hexa-hydrophtalic, and the like, with polymethylol alkanes, such as trimethylolethane, trimethylolpropane, pentaerytritol and the like. In the second stage of the reaction the polycarboxylic acid formed in the first stage forms an adduct with glycidyl methacrylate.

For example, the basic monomer is obtained by reacting the following tricomponent mixture: hexahydrophtalic anhydride, 1,1,1-tris-hydroxymethylethane and glycidylmethacrylate. These components must be reacted in molecular proportions of 3:1:3 respectively. Reaction is carried out in a nitrogen atmosphere in the presence of an electron donating catalyst, such as a tertiary amine, and an inhibitor such as hydroquinone. At the first stage of reaction of the anhydride with 1,1,1-tris-hydroxymethylethane forms a the trimer, containing three carboxylic groups. In the second stage mentioned above, reaction of tricarboxylic acid with glycidylmethacrylate forms the adduct containing three methacrylic groups. Two clear stages cannot be observed if the reaction is carried out with three components loaded simultaneously. The procedure may be continued until almost 100% of the components are taken up in the reaction.

The obtained product is a viscous liquid like BIS-GMA, which may be diluted with low viscosity methacrylic monomers such as, diethylenglycol dimethacrylate, triethylenglycol dimethacrylate, 1,6-hexamethylenglycol dimethacrylate, and the like, and may be used as a polymer matrix in dental compositions.

The presence of the three hydroxyl groups per molecule do not make water sorption higher than permitted by ADA Spec. No. 27. All other characteristics of the composition indicate a high utility as a dental restorative material. The presence of three hydroxyl groups contributes to the high viscosity of the monomer, which is avoided in the monomer of Formula (2) obtained by transesterification of the monomer of Formula (1) with methylmethacrylate in the presence of a tindibutyl diacetate catalyst.

Polymerization of the methacrylate monomers of the present invention may be carried out by any convenient method, using either chemical or photochemical initiation. Thus, in order to induce curing of polymethacrylate monomers, a free radical catalyst may be placed therein. Organic peroxide and hydroperoxide initiators, such as methyl ethyl ketone peroxide, tert-butyl peroctoate, isopropyl percarbonate, cumene hydroperoxide, dicumyl peroxide and especially benzoyl peroxide are preferred.

In the curing process, the initiator works in conjunction with activators or accelerators such as, tertiary aromatic amines N,N-dimethyl-o-toludine or N,N-bis(2-hydroxyethyl)p-toludine, pentaerytritol tetra-(3-mercaptopropionate). The amount of catalyst depends upon the needed curing rate and may be selected from about 0.5% to about 4.0% by weight of the polymerizable components. As with the free radical catalyst, the amount of the activator selected may vary from about 0.4 to about 4.0% by weight of the polymerizable components, depending upon desired curing rate.

Polymerization of the methacrylates of the present invention may also be initiated by a variety of ultraviolet or visible light means, using known light activated polymerization initiators such as DL Camphorquinone, benzoin, benzil, and the like, as well as the above photoinitiators used with activators such as tertiary aliphatic or aromatic amines like N,N,N,N,-tetramethylenediamine (TEMED) dimethylaminothylmethacrylate (Ageflax-FM-1).

The amount of initiator, preferably about 0.08–0.24% and of activator, preferably about 0.1–0.5% by weight of the polymerizable components, depend upon the thickness of sample and the desired curing rate. The amount of tertiary amine used as a catalyst in the main reaction and left in the monomer may be calculated.

A composite restorative material is a composite material comprising a polymerizable material and a suitable filler. These materials must be capable of curing in situ on teeth to restore a hardened surface thereto, and are generally applied as a filling material to prepared or drilled teeth. Accordingly, composite restorative materials should have a thick, workable consistency suitable for application to a prepared tooth and capable of being shaped or molded thereon before setting occurs. Particularly preferred inorganic filler materials include silica materials (i.g. powdered quartz, barium glasses, borsilica, and strontium silica glasses, Sio2, fumed silica, precipitate and colloidal silica).

There are commercially available a few types of composite materials which depend upon the type of filler used in compositions. These include large particle composites (size of particles 15–30 mk), microfill composites (size of particles 0.04 mk), fine particle composites (size of particles 1–8 mk), blended composites (size of particles 0.04–5.0 mk).

The amount of filler depends upon the type of compositions and may vary from about 51–53% by weight for microfill composites to 79% and more for other types of composites.

EXAMPLES

While the present invention has been described above, the details of the invention will be better understood by reference to the following examples:

EXAMPLE I 49.2 gr of hexahydrophtalic anhydrid, 12.0 gr of 1,1,1-tris-hydroxymethyl ethane (trimethylolethane) and 42.6 gr of glycidil methacrylate were placed in a three throat flask provided with a condenser and an agitator. Reaction was carried out in the presence of 0.6 gr of N,N-diethylethanol amine as a catalyst and 0.03 gr of hydroquinone as an inhibitor. The reaction mixture was maintained at a temperature of 85° C. in nitrogen atmosphere with good mixing. After 2.5 hours the temperature was raised to 95° C. and after two more hours it was raised again to 100° C. The reaction mixture was kept at this temperature for one more hour. The residue was a colorless or lightly yellow, viscous liquid with a chemical structure in accordance with Formula (1).

EXAMPLE II 30.0 gr of the final monomer product of Example I and 30.0 gr of methylmethacrylate were placed in a flask provided with a condenser and an agitator. A transesterification reaction was carried out in the presence of M & T Fascat 4200 catalyst (0.1 gr) and 0.02 gr hydroquinone as inhibitor in a nitrogen atmosphere at 85° C. The reaction mixture was maintained at this temperature for one hour with good mixing and then the temperature was raised to 105° C. Because the reaction mixture is not boiled, mixing was continued for one more hour. At this time, the condenser was changed for straight distillation and excess of methymethacrylate with methanol distilled from reaction mixture with use of vacuum.

The residue is a colorless or slightly yellow viscous liquid which had to be diluted with low viscosity dimethacrylates, such as triethylenglycol dimethacrylates in proportions 1:1 to 2:1 and more. This diluted residue, which has the chemical structure represented by Formula (2), was suitable for use as a binder in restorative dental compositions.

EXAMPLE III-IV

A polymer matrix of each of the compositions of Examples I and II, respectively, was prepared by diluting each of the methacrylic monomers in triethylenglycoldimethacrylate in weight ratios of from of 2.0:1 to 1:1.

Each polymer matrix was prepared for a light curing process and contained 0.15% wt. of camphorquinone as photoinitiator and 0.5% wt. of dimethylaminothylmethacrylate as an activator of polymerization and 0.05% wt. 2,6-di-tert-butyl-4-methylphenol as an inhibitor.

Radiopaque dental filler strontium silica glass type IX-2405 "R", having a particle size of 7-22 mk, produced by Innotech Glass Division Co. was used in each of the compositions of the present invention as a filler after preliminary silanization with 3-methacryloxypropyltrimethoxy silane of Dow Corning (Z-6030). Specimens of each cured composition containing monomers according to the present invention exhibited desirable properties and were capable of holding up under strong mastication forces.

Table 1 provides data showing the physical characteristics of a cured sample of each of the preferred compositions of Examples III and IV, respectively.

TABLE I

| Property | Composition of Example III | Composition of Example IV |
|---|---|---|
| Hardness Barcol for a 3.5 mm thick upper-bottom side specimen | 97–92 | 95–93 |
| Water sorption in mg per 1 cm$^2$ | Type I (unfilled) 1.37 | Type I (unfilled) 1.0 |
| Surface after one week, 37° C. | Type II (unfilled) 0.7 | Type II (unfilled) 0.4 |
| Shrinkage linear in % | 0.168 | 0.253 |

These results are well within the standards, as set out in Specification N27 of ADA.

All of the characteristics of the compositions of the present invention demonstrate a high degree of utility as a dental restorative material.

While the invention has been described with respect to various specific examples and embodiments, it is to be understood that the invention is not limited thereto and that it can be variously practiced within the scope of the following claims.

What is claimed is:

1. A polyfunctional methacrylate selected from the group comprising compositions having the following chemical formulas:

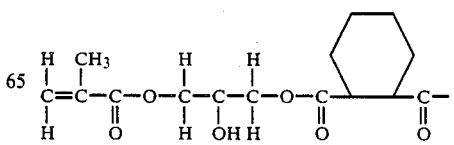

-continued

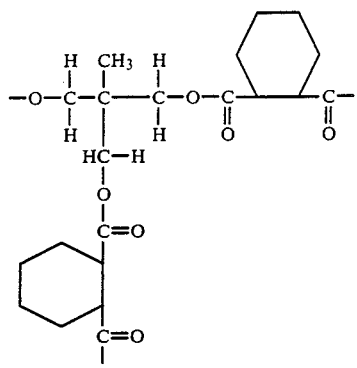

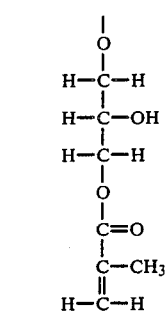

and

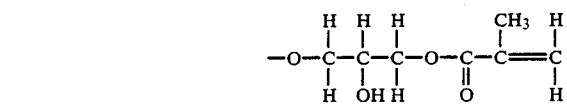

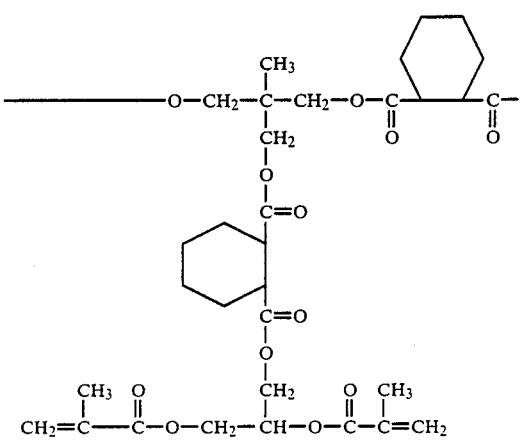

-continued

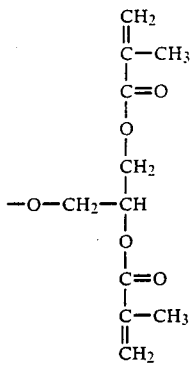

as a binder material in a dental restorative composition in combination with a filler which is at least about 51% by weight of the composition.

2. A polyfunctional methacrylate according to claim 1 wherein the methacrylate used is that of Formula (1).

3. A polyfunctional methacrylate according to claim 1 wherein the methacrylate used is that of Formula (2).

4. A dental restorative composition comprising an inorganic filler which is at least about 51% by weight of the composition and at least one polymerizable polyfunctional methacrylate selected from the group comprising compositions having the following chemical formulas:

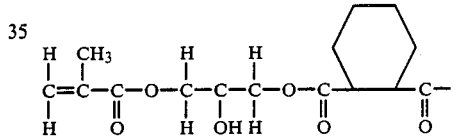

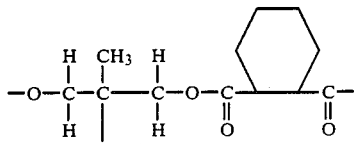

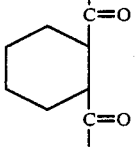

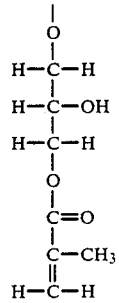

-continued

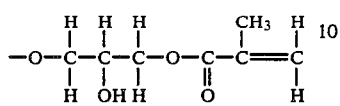

and

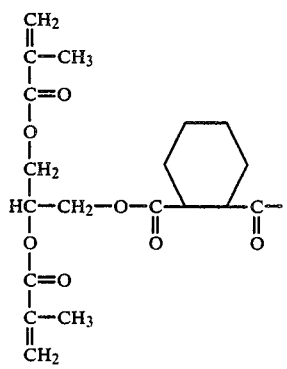

-continued

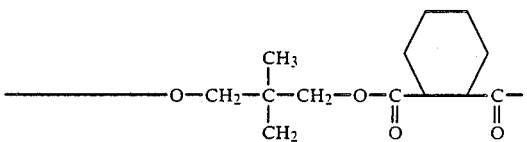

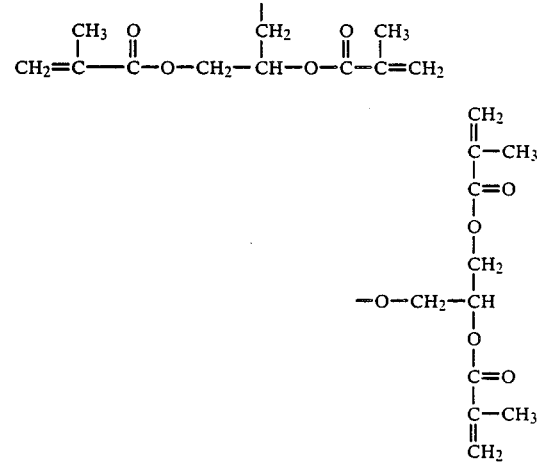

5. A dental restorative composition according to claim 4 wherein the inorganic filler is selected from the group comprising fused silica, silica glass and crystalline quartz.

6. A dental restorative composition according to claim 5 which also comprises one or more additives for the initiation of the polymerization reaction thereof.

7. A dental restorative composition according to claim 5 which also comprises one ore more additives for the inhibition of the polymerization reaction thereof.

8. A dental restorative composition according to claim 6 which is capable of being cured via exposure to a visual light source.

* * * * *